US012613108B2

(12) United States Patent
Feingold et al.

(10) Patent No.: US 12,613,108 B2
(45) Date of Patent: Apr. 28, 2026

(54) BUTTON PRESS DETECTION SYSTEM

(71) Applicant: Stryker Corporation, Kalamazoo, MI (US)

(72) Inventors: Benjamin Hyman Feingold, San Francisco, CA (US); Robert L. Jones, III, South Bend, IN (US); Wenjie Deng, San Jose, CA (US)

(73) Assignee: Stryker Corporation, Portage, MI (US)

( * ) Notice: Subject to any disclaimer, the term of this patent is extended or adjusted under 35 U.S.C. 154(b) by 339 days.

(21) Appl. No.: 18/528,508

(22) Filed: Dec. 4, 2023

(65) Prior Publication Data

US 2024/0192025 A1 Jun. 13, 2024

Related U.S. Application Data

(60) Provisional application No. 63/386,884, filed on Dec. 9, 2022.

(51) Int. Cl.
*G01D 5/12* (2006.01)
*A61B 1/00* (2006.01)

(52) U.S. Cl.
CPC .............. *G01D 5/12* (2013.01); *A61B 1/0004* (2022.02)

(58) Field of Classification Search
CPC ....................................................... G01D 5/12
See application file for complete search history.

(56) References Cited

U.S. PATENT DOCUMENTS

| | | | | |
|---|---|---|---|---|
| 4,691,185 | A | * | 9/1987 | Loubier .................... G01F 1/24 |
| | | | | 324/207.13 |
| 5,691,637 | A | * | 11/1997 | Oswald .................. G01B 7/004 |
| | | | | 324/207.2 |
| 6,854,566 | B2 | | 2/2005 | Sweet et al. |
| 8,267,921 | B2 | * | 9/2012 | Yodfat ................ A61M 5/1424 |
| | | | | 604/93.01 |
| 10,263,171 | B2 | * | 4/2019 | Wiener .............. A61B 18/1206 |
| 2005/0059858 | A1 | | 3/2005 | Frith et al. |
| 2014/0184367 | A1 | | 7/2014 | Liao |
| 2017/0296183 | A1 | * | 10/2017 | Shelton, IV ..... A61B 17/07207 |
| 2021/0271330 | A1 | | 9/2021 | Heni et al. |
| 2021/0293901 | A1 | * | 9/2021 | Dupre ................ G01R 33/0082 |
| 2024/0108421 | A1 | * | 4/2024 | Shelton, IV .......... H02K 7/145 |

* cited by examiner

*Primary Examiner* — Walter L Lindsay, Jr.
*Assistant Examiner* — Milton Gonzalez
(74) *Attorney, Agent, or Firm* — Morrison & Foerster LLP

(57) ABSTRACT

Disclosed herein are systems and methods for accurately detecting button presses and/or button releases on a keypad of a camera such as an endoscopic camera head. A button press and/or a button release may be detected by determining a change in the sensor voltage output from a magnetic field sensor and identifying a spike in the sensor voltage change. A spike occurs when the slope of the sensor voltage has a magnitude that is greater than a slope threshold, and indicates a button press and/or a button release. Aspects of the disclosure comprise a controller that identifies a spike. The controller may identify a second spike and determine the type of button press based on the duration between the first spike and the second spike. The disclosed systems and methods may further include and apply to a keypad comprising a plurality of buttons, such as closely-spaced buttons and concentric buttons.

20 Claims, 11 Drawing Sheets

250

240

350

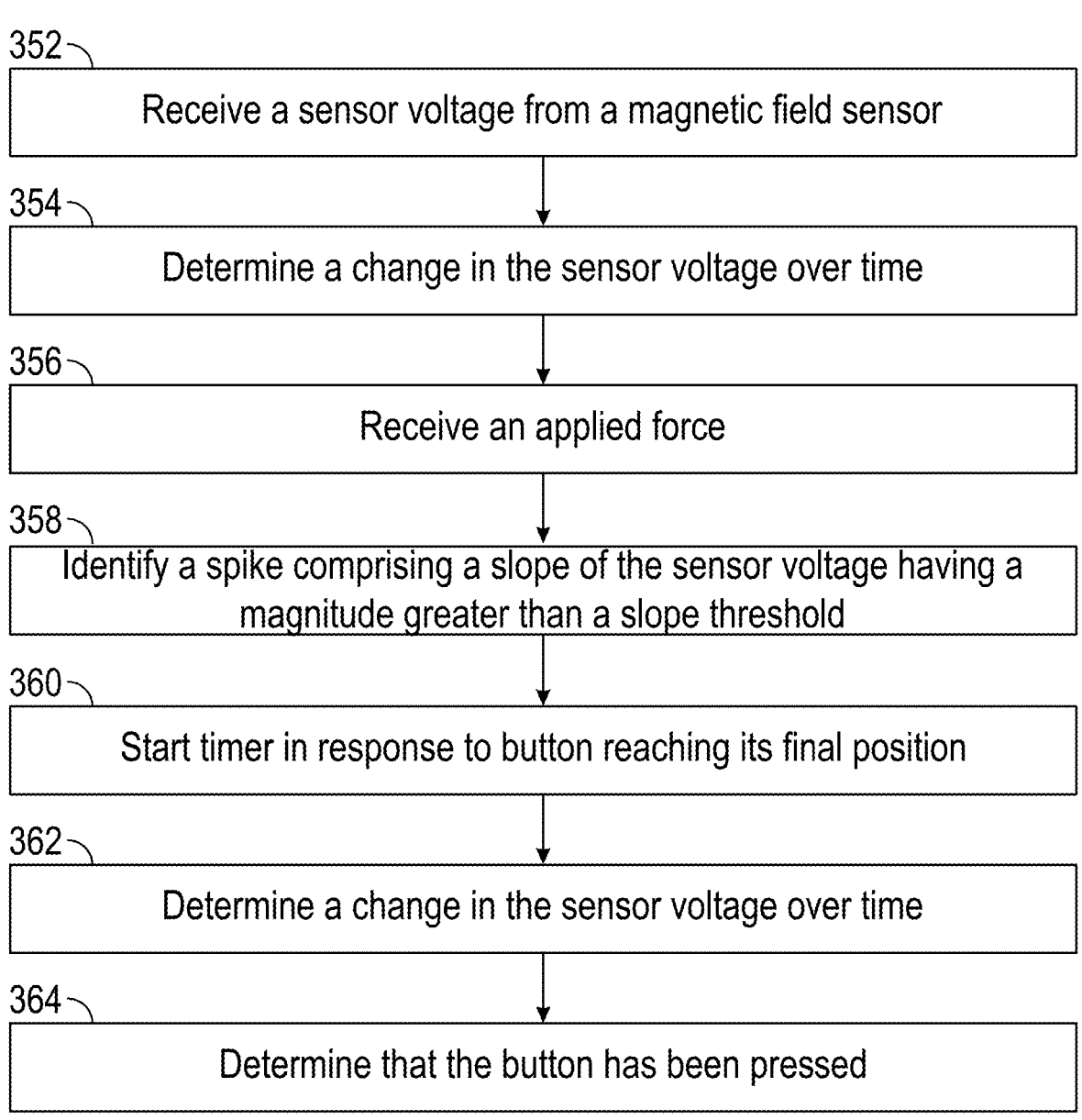

352

Receive a sensor voltage from a magnetic field sensor

354

Determine a change in the sensor voltage over time

356

Receive an applied force

358

Identify a spike comprising a slope of the sensor voltage having a magnitude greater than a slope threshold

360

Start timer in response to button reaching its final position

362

Determine a change in the sensor voltage over time

364

Determine that the button has been pressed

BUTTON PRESS DETECTION SYSTEM

CROSS-REFERENCE TO RELATED APPLICATIONS

This application claims the benefit of U.S. Provisional Application No. 63/386,884, filed Dec. 9, 2022, the entire contents of which are hereby incorporated by reference herein.

FIELD

The present invention relates to button press detection, particularly for an endoscopic system.

BACKGROUND

An endoscope is a surgical tool designed to be placed inside a human body in order to provide a view of the interior portion of the human body. In endoscopic surgery, the endoscope is placed in the human body at the location where it is necessary to perform a surgical procedure. Other surgical instruments are placed in the human body at the surgical site. The user (e.g., surgeon, medical staff, etc.) views the surgical site through the endoscope in order to assess the interior portion of the human body and to manipulate other surgical instruments to perform the desired surgical procedure. The development of endoscopes and their companion surgical instruments has made it possible to perform minimally invasive surgery that eliminates the need to make a large incision in the human body to gain access to the surgical site. Instead, during endoscopic surgery, small openings, called portals, are formed. One advantage of performing endoscopic surgery is that since the portions of the human body that are cut are smaller, the portions of the human body that need to heal after the surgery are also small. Still another advantage of endoscopic surgery is that it exposes less of the internal tissue of the human body to the open environment. This minimal opening of the human body lessens the extent to which the internal tissue and organs of the human body are open to infection.

During endoscopic surgery, the user may control one or more functions of the endoscopic system using buttons. For example, the user may depress a button for activating a light source or capturing a picture of the interior portion of the human body being assessed. The user may need to be able to reliably control the endoscopic system, such as reliably activate and deactivate the light source of the endoscope, reliably capture pictures or videos, etc. Any complications with controlling the endoscopic system may cause frustration to the user and create an unsafe situation because the user (e.g., surgeon, medical staff, etc.) may be required to perform the surgical procedure without complete functionality. Button presses must be accurately detected, and phantom button presses (e.g., when a button has not been pressed or released, but the button press detection system registers a button press or release; or when a button has been pressed or released, but the button press detection system does not register the button press or release) must be minimized.

SUMMARY

According to various aspects, systems and methods include accurately detecting button presses and/or button releases on a keypad of a camera such as an endoscopic camera head. A button press and/or a button release may be detected by determining a change in the sensor voltage output from a magnetic field sensor and identifying a spike in the sensor voltage change. A spike occurs when the slope of the sensor voltage has a magnitude that is greater than a slope threshold. A spike indicates a button press and/or a button release. Aspects of the disclosure comprise a controller that identifies a (first) spike. In some aspects, the controller identifies a second spike and determines the type of button press based on the duration between the first spike and the second spike. The disclosed systems and methods may further include and apply to a keypad comprising a plurality of buttons, such as closely-spaced buttons and concentric buttons.

According to some examples, a method of detecting a button press and/or a button release of a button on a camera head comprises: receiving a sensor voltage from a magnetic field sensor; determining a change of the sensor voltage over time; and identifying a spike comprising a slope of the sensor voltage having a magnitude greater than a slope threshold, wherein the spike indicates the button press and/or the button release.

In any of the examples, the method further comprises: registering the button press when the slope of the sensor voltage has a first orientation.

In any of the examples, the method further comprises: registering the button release when the slope of the sensor voltage has a second orientation.

In any of the examples, the spike occurs when the button is between an intermediate position and a final position.

In any of the examples, the spike occurs when a magnet associated with the button has a high velocity.

In any of the examples, the spike occurs when a dome associated with the button has a low level of resistance, the dome comprising the low level of resistance and a high level of resistance.

In any of the examples, the method further comprises: identifying a low slope of the sensor voltage comprising a non-zero magnitude less than the slope threshold, wherein the low slope does not indicate the button press and/or the button release.

In any of the examples, the method further comprises: identifying a low slope of the sensor voltage comprising a non-zero magnitude less than the slope threshold, wherein the low slope occurs when a dome associated with the button has a high level of resistance, the dome comprising a low level of resistance and the high level of resistance.

In any of the examples, the method further comprises: identifying a low slope of the sensor voltage comprising a non-zero magnitude less than the slope threshold, wherein the low slope occurs when a magnet associated with the button has a low velocity.

In any of the examples, the method further comprises: identifying a low slope of the sensor voltage comprising a non-zero magnitude less than the slope threshold, wherein the low slope occurs when the button is between an initial position and an intermediate position.

In any of the examples, the method further comprises: determining a position of the button based on the slope of the sensor voltage.

In any of the examples, the method further comprises: determining a position of the button based on the slope of the sensor voltage, wherein the position of the button comprises an initial position, an intermediate position, and a final position.

In any of the examples, the method further comprises: providing tactile feedback at an intermediate position of the button.

In any of the examples, the method further comprises: determining a position of the button as being a final position based on the slope of the sensor voltage; and starting a timer when the button is in the final position.

In any of the examples, the method further comprises: registering the button press when the slope of the sensor voltage has a first orientation and the spike is identified.

In any of the examples, the method further comprises: registering the button press when the slope of the sensor voltage has a first orientation and the button is in a final position.

In any of the examples, the method further comprises: identifying a second spike in the sensor voltage change, wherein the second spike comprises the slope of the sensor voltage having a magnitude greater than the slope threshold and a second orientation; and registering the button press when a duration between the spike and the second spike is less than a duration threshold corresponding to a type of button press.

In any of the examples, the method further comprises: identifying a second spike in the sensor voltage change, wherein the second spike comprises the slope of the sensor voltage having a magnitude greater than the slope threshold and a second orientation; and registering the button press as a short press when a duration between the spike and the second spike is shorter than a short press duration threshold.

In any of the examples, the method further comprises: identifying a second spike in the sensor voltage change, wherein the second spike comprises the slope of the sensor voltage having a magnitude greater than the slope threshold and a second orientation; and registering the button press as a short press when a duration between the spike and the second spike is shorter than 50 milliseconds.

In any of the examples, the method further comprises: identifying a second spike in the sensor voltage change, wherein the second spike comprises the slope of the sensor voltage having a magnitude greater than the slope threshold and a second orientation; and registering the button press as a long press when a duration between the spike and the second spike is longer than a short press duration threshold and shorter than a long press duration threshold.

In any of the examples, the method further comprises: identifying a second spike in the sensor voltage change, wherein the second spike comprises the slope of the sensor voltage having a magnitude greater than the slope threshold and a second orientation; and registering the button press as a long press when a duration between the spike and the second spike is between 50-500 milliseconds.

In any of the examples, the method further comprises: identifying a second spike in the sensor voltage change, wherein the second spike comprises the slope of the sensor voltage having a magnitude greater than the slope threshold and a second orientation; and registering the button press as a press-and-hold press when a duration between the spike and the second spike is longer than a long press duration threshold.

In any of the examples, the method further comprises: identifying a second spike in the sensor voltage change, wherein the second spike comprises the slope of the sensor voltage having a magnitude greater than the slope threshold and a second orientation; and registering the button press as a press-and-hold press when a duration between the spike and the second spike is longer than a 500 milliseconds.

In any of the examples, the method further comprises: registering the button release when the slope of the sensor voltage has a second orientation and the spike is identified.

In any of the examples, the method further comprises: registering the button release when the slope of the sensor voltage has a second orientation and the button is in an initial position.

In any of the examples, the method further comprises: dynamically adjusting the slope threshold.

In any of the examples, the camera head comprises a plurality of buttons, each of the plurality of buttons is associated with independent receiving, determining, and identifying steps.

In any of the examples, the camera head comprises a first button and a second button, the method further comprising: determining whether the button press corresponds to the first button or the second button based on an orientation of the slope of the sensor voltage.

In any of the examples, the magnetic field sensor is configured to detect positive magnetic flux and negative magnetic flux.

In any of the examples, the camera head comprises a first button and a second button, the method further comprising: determining whether the button press and/or the button release corresponds to the first button or the second button based on the slope of the sensor voltage.

In any of the examples, the camera head is included in an endoscopic system.

According to some examples, a system comprising a camera head; a button; a magnet; a magnetic field sensor that outputs a sensor voltage indicative of magnetic flux between the magnet and the magnetic field sensor; and a controller that: determines a change of the sensor voltage over time; and identifies a spike in the sensor voltage change, wherein the spike comprises a slope of the sensor voltage having a magnitude greater than a slope threshold, wherein the spike indicates a button press and/or a button release.

In any of the examples, the controller further: registers the button press when the slope of the sensor voltage has a first orientation.

In any of the examples, the controller further: registers the button release when the slope of the sensor voltage has a second orientation.

In any of the examples, the spike occurs when the button is between an intermediate position and a final position.

In any of the examples, the spike occurs when the magnet has a high velocity.

In any of the examples, the system further comprises: a dome located between the magnet and the magnetic field sensor, the dome comprising a low level of resistance and a high level of resistance.

In any of the examples, the system further comprises: a dome located between the magnet and the magnetic field sensor, the dome comprising a low level of resistance and a high level of resistance, wherein the spike occurs when the dome has the low level of resistance.

In any of the examples, the system further comprises: a dome located between the magnet and the magnetic field sensor, the dome comprising a low level of resistance and a high level of resistance; wherein the controller further: identifies a low slope of the sensor voltage comprising a non-zero magnitude less than the slope threshold, and the low slope occurs when the dome has the high level of resistance.

In any of the examples, the controller further: identifies a low slope of the sensor voltage comprising a non-zero magnitude less than the slope threshold, and the low slope occurs when the magnet has a low velocity.

In any of the examples, the controller further: identifies a low slope of the sensor voltage comprising a non-zero magnitude less than the slope threshold, wherein the low slope occurs when the button is between an initial position and an intermediate position.

In any of the examples, the button comprises a plurality of positions determined based on the slope of the sensor voltage.

In any of the examples, the button comprises a plurality of positions determined based on the slope of the sensor voltage, where the plurality of positions comprises an initial position, an intermediate position, and a final position.

In any of the examples, the button provides tactile feedback at an intermediate position.

In any of the examples, the controller further: determines a position of the button as being a final position based on the slope of the sensor voltage; and starts a timer when the button is in the final position.

In any of the examples, the controller further: registers the button press when the slope of the sensor voltage has a first orientation and the spike is identified.

In any of the examples, the controller further: registers the button press when the slope of the sensor voltage has a first orientation and the button is in a final position.

In any of the examples, the controller further: identifies a second spike in the sensor voltage change, wherein the second spike comprises the slope of the sensor voltage having a magnitude greater than the slope threshold and a second orientation; and registers the button press when a duration between the spike and the second spike is less than a duration threshold corresponding to a type of button press.

In any of the examples, the controller further: identifies a second spike in the sensor voltage change, wherein the second spike comprises the slope of the sensor voltage having a magnitude greater than the slope threshold and a second orientation; and registers the button press as a short press when a duration between the spike and the second spike is shorter than a short press duration threshold.

In any of the examples, the controller further: identifies a second spike in the sensor voltage change, wherein the second spike comprises the slope of the sensor voltage having a magnitude greater than the slope threshold and a second orientation; and registers the button press as a short press when a duration between the spike and the second spike is shorter than 50 milliseconds.

In any of the examples, the controller further: identifies a second spike in the sensor voltage change, wherein the second spike comprises the slope of the sensor voltage having a magnitude greater than the slope threshold and a second orientation; and registers the button press as a long press when a duration between the spike and the second spike is longer than a short press duration threshold and shorter than a long press duration threshold.

In any of the examples, the controller further: identifies a second spike in the sensor voltage change, wherein the second spike comprises the slope of the sensor voltage having a magnitude greater than the slope threshold and a second orientation; and registers the button press as a long press when a duration between the spike and the second spike is between 50-500 milliseconds.

In any of the examples, the controller further: identifies a second spike in the sensor voltage change, wherein the second spike comprises the slope of the sensor voltage having a magnitude greater than the slope threshold and a second orientation; and registers the button press as a press-and-hold press when a duration between the spike and the second spike is longer than a long press duration threshold.

In any of the examples, the controller further: identifies a second spike in the sensor voltage change, wherein the second spike comprises the slope of the sensor voltage having a magnitude greater than the slope threshold and a second orientation; and registers the button press as a press-and-hold press when a duration between the spike and the second spike is longer than 500 milliseconds.

In any of the examples, the controller further: registers the button release when the slope of the sensor voltage has a second orientation and the spike is identified.

In any of the examples, the controller further: registers the button release when the slope of the sensor voltage has a second orientation and the button is in an initial position.

In any of the examples, the controller further: dynamically adjusts the slope threshold.

In any of the examples, the camera head comprises a plurality of buttons, each of the plurality of buttons is associated with a unique sensor voltage.

In any of the examples, the camera head comprises a first magnet and a second magnet, the first magnet having a first polarity opposite from a second polarity of the second magnet.

In any of the examples, the magnetic field sensor is configured to detect positive magnetic flux and negative magnetic flux.

In any of the examples, the camera head comprises a first button and a second button, wherein the controller further: determines whether the button press and/or the button release corresponds to the first button or the second button based on the slope of the sensor voltage.

In any of the examples, the camera head comprises one or more buttons and one or more magnetic field sensors, wherein a number of the one or more buttons is the same as a number of the one or more magnetic field sensors.

In any of the examples, the camera head comprises a plurality of buttons and one or more magnetic field sensors, wherein a number of the plurality of buttons is greater than a number of the one or more magnetic field sensors.

In any of the examples, the camera head comprises one or more buttons and one or more domes, wherein a number of the one or more buttons is the same as a number of the one or more domes.

In any of the examples, the camera head comprises a plurality of buttons and one or more domes, wherein a number of the plurality of buttons is greater than a number of the one or more domes.

In any of the examples, the camera head comprises a plurality of buttons, a plurality of magnets, and a plurality of domes, wherein the plurality of buttons, the plurality of magnets, and the plurality of domes are associated with the magnetic field sensor.

In any of the examples, the camera head comprises a first button and a second button, wherein the first button is an inner button and the second button is an outer button.

In any of the examples, the camera head comprises a first magnet and a second magnet, wherein the first magnet is an inner magnet and the second magnet is an outer magnet.

In any of the examples, the camera head comprises a first magnet and a second magnet, wherein the first magnet is an inner magnet and the second magnet is an outer magnet, wherein the inner magnet has a different magnetic force than the outer magnet.

In any of the examples, the camera head comprises a plurality of buttons, a plurality of magnets, and a dome, wherein the plurality of buttons, the plurality of magnets, and the dome are associated with the magnetic field sensor.

In any of the examples, the system is an endoscopic system.

In any of the examples, the system further comprises: a camera enclosure, wherein the camera head is located outside of the camera enclosure.

In any of the examples, the system further comprises: a camera enclosure comprising circuitry for the camera head.

It will be appreciated that any of the variations, aspects, features, and options described in view of the systems apply equally to the methods and vice versa. It will also be clear that any one or more of the above variations, aspects, features, and options can be combined.

BRIEF DESCRIPTION OF THE FIGURES

The invention will now be described, by way of example only, with reference to the accompanying drawings, in which:

FIG. 3B illustrates a flowchart of an example method for detecting a button press on a keypad of a camera head, according to some aspects.

DETAILED DESCRIPTION

Figure 1:
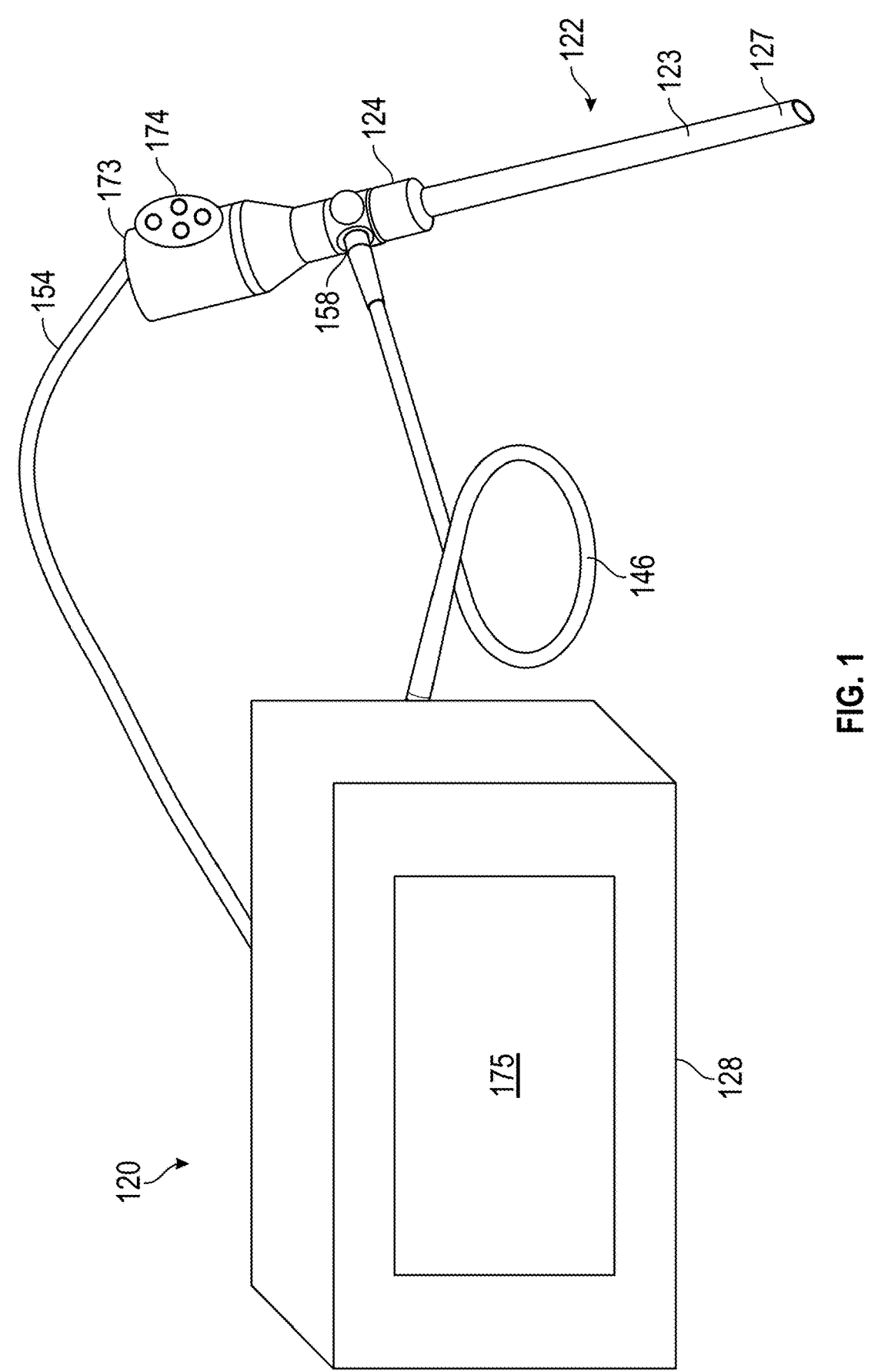
FIG. 1 illustrates an example endoscopic system, according to some aspects.

Reference will now be made in detail to implementations and various aspects and variations of systems and methods described herein. Although several example variations of the systems and methods are described herein, other variations of the systems and methods may include aspects of the systems and methods described herein combined in any suitable manner having combinations of all or some of the aspects described.

Systems and methods according to the principles described herein detect button presses and/or button releases based on a non-zero slope in the sensor voltage output by a magnetic field sensor. A slope having a magnitude greater than a slope threshold indicates a button press and/or a button release. In some aspects, a slope having a first orientation indicates a button press, and a slope having a second orientation indicates a button release. The second orientation may be opposite from the first orientation. As one non-limiting example, the first orientation corresponds to a positive slope, and the second orientation corresponds to a negative slope. As another non-limiting example, in some instances (e.g., based on the polarity of the magnet), the first orientation corresponds to a negative slope, and the second orientation corresponds to a positive slope. The disclosed buttons comprise one or more magnets, one or more domes, and one or more magnetic field sensors. The sensor voltage output from a magnetic field sensor is based on the distance between a magnet and the magnetic field sensor, and the slope of the sensor voltage is based on the velocity of the magnet's movement toward or away from the magnetic field sensor. A higher sensor voltage occurs when the magnet is closer to the magnetic field sensor, and a lower sensor voltage occurs when the magnet is further away. A high slope of the sensor voltage occurs when the magnet is moving rapidly, such as during a button press and/or a button release. This high slope is identified as a spike. A low slope of the sensor voltage occurs when the magnet is moving slowly, such as for a phantom button press (e.g., when a user has not pressed or released a button, but the magnet moves slightly closer to or away from the magnetic field sensor due to the camera head being dropped).

In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating," or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general-purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMS, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. Suitable processors include central processing units (CPUs), graphical processing units (GPUs), field-programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1 illustrates an example endoscopic system, according to some aspects. The endoscopic system 120 includes an endoscope 122, transmission cables 146 and 154, and a control unit 128. The endoscope 122 is an elongated and generally hollow shaft 123 with a distal end 127 configured for insertion within an interior portion of a human body. The hollow shaft 123 also has a proximal end 124 for mounting a camera head 173. The camera head 173 provides a viewing port through which a camera allows the user to view the surgical field (for example, through a connection between a viewing port, a digital camera, and a display screen 175). The camera head 173 comprises a keypad 174, which includes a plurality of buttons. The plurality of buttons, when pressed, transmits a signal through cable 154, allowing the user to control one or more functions of the endoscopic system 120. A light port 158 may be connected with a light source to selectively transmit light to a target via the endoscope 122.

Figure 2A:
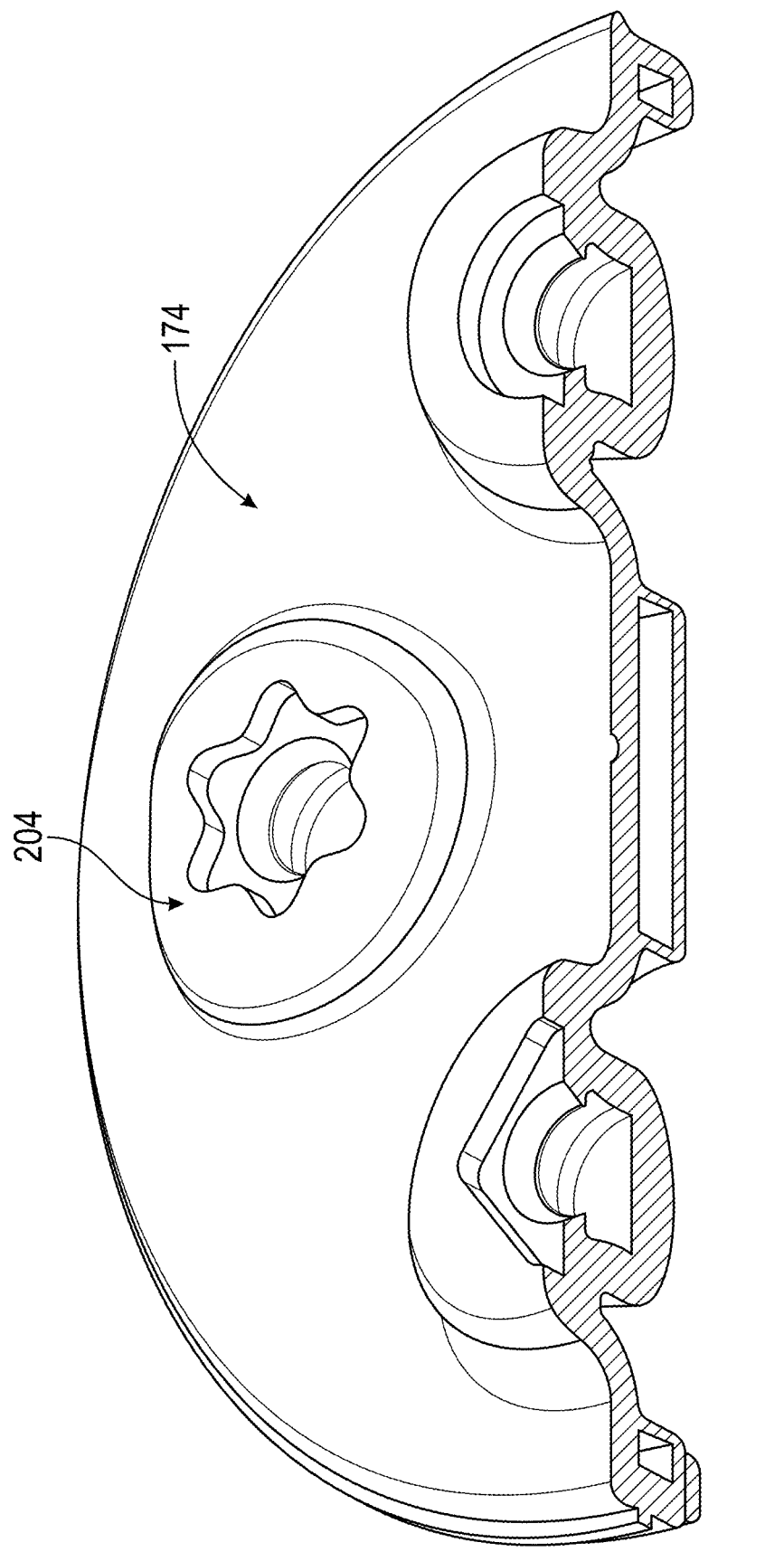
FIGS. 2A-2C illustrate views of an example keypad of a camera head, according to some aspects.
Figure 2B:
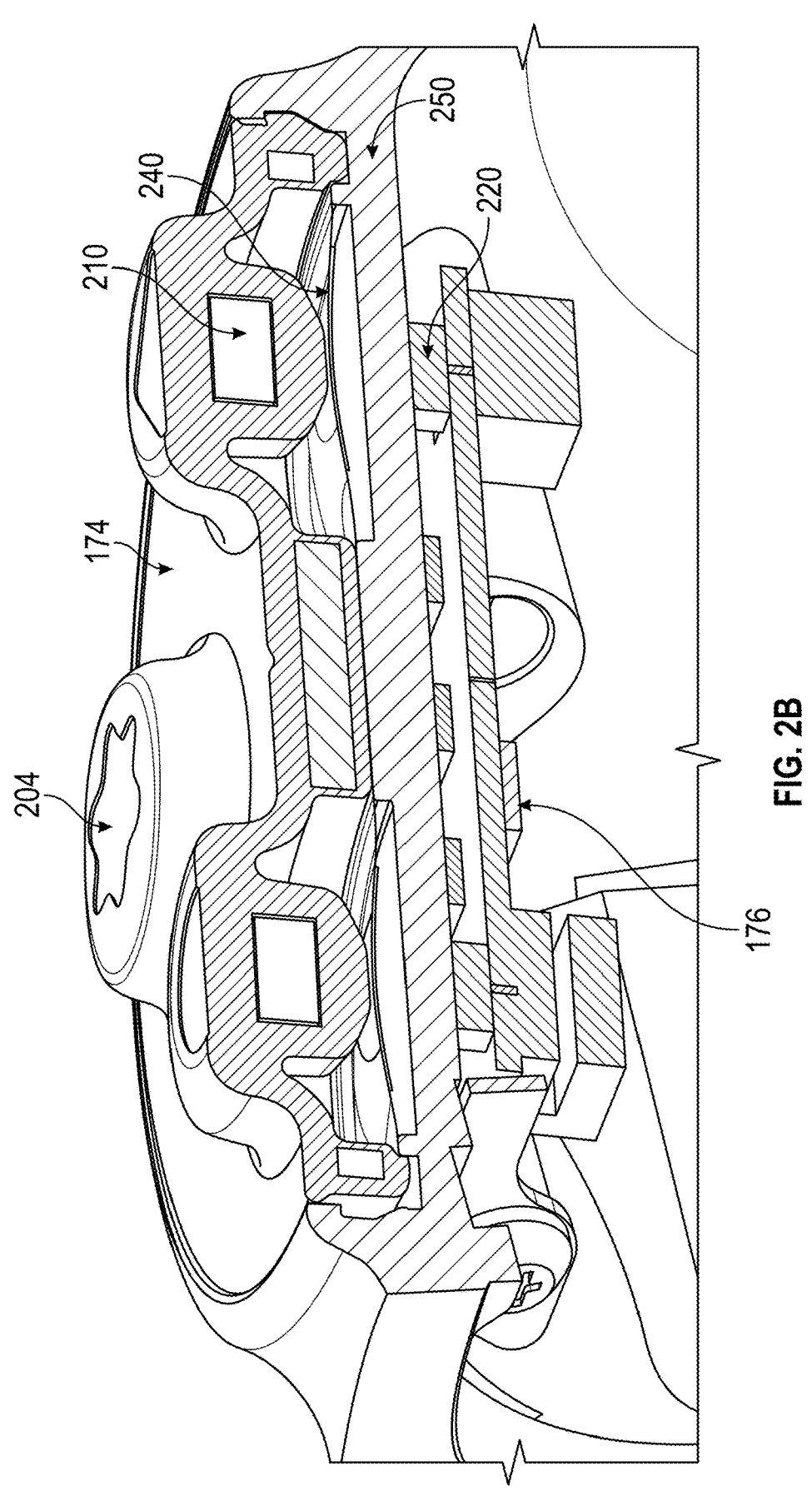
Figure 2C:

FIG. 2A-2C illustrate views of an example keypad 174 of a camera head 173, according to some aspects. As shown in FIG. 2A, the keypad 174 comprises one or more buttons 204 for allowing a user (e.g., surgeon, medical staff, etc.) to control one or more functions of the endoscopic system 120. The keypad 174 comprises any number of buttons 204 including, but not limited to, 1, 2, 3, 4, 5, 6, etc.

As shown in FIG. 2B, the buttons 204 include one or more magnets 210 located within one or more cavities of the keypad 174. In some aspects, the keypad 174 is formed using a molding process, such as a multi-part molding process that involves forming the bottom of the keypad 174 including the cavities, inserting the magnets 210 into the cavities, and forming the top of the keypad 174 over the magnets 210. The top and bottom of the keypad 174 may comprise rubber or silicone, for example.

A button 204 comprises a magnet 210 and a corresponding magnetic field sensor 220. In some aspects, the number of buttons 204 may be equal to the number of magnetic field sensors 220. In other aspects, the number of buttons 204 may be greater than the number of magnetic field sensors 220 (discussed in more detail below). A button press from, e.g., the user's finger causes the magnet 210 to move toward the magnetic field sensor 220. A button release from, e.g., the user's finger causes the magnet to move away from the magnetic field sensor 220. The magnetic field sensor 220 measures the amount of magnetic flux and outputs a sensor voltage corresponding to the measured amount of magnetic flux from the magnet 210. As one non-limiting example, the magnetic field sensor 220 comprises a Hall effect sensor.

In some aspects, the magnetic field sensor 220 outputs a sensor voltage indicative of the amount of magnetic flux between the magnet 210 and the magnetic field sensor 220. The relationship between the sensor voltage and distance between the magnetic field sensor 220 and magnet 210 may be linear. Depending on the polarity of the magnet 210, the sensor voltage may increase or decrease as the magnet 210 approaches the magnetic field sensor 200. Similarly, the sensor voltage may increase or decrease as the magnet 210 moves further away from the magnetic field sensor 220. The sensor voltage may be higher when the magnet 210 is closer to the magnetic field sensor 220. In some aspects, the sensor voltage is lowest when the button 204 is in the initial position, highest when in the final position, and has a voltage between lowest and highest when in the intermediate position. For example, the sensor voltage may be 0 V when the button 204 is in the initial position, 0.5 V when the button 204 is in the intermediate position, and 1 V when the button 204 is in the final position.

In some instances (depending on the polarity of the magnet 210), the sensor voltage may be lower when the magnet 210 is closer to the magnetic field sensor 220. The sensor voltage may be highest, such as 1V, when the button 204 is in the initial position, lowest, such as 0 V, when in the final position, and has a voltage between lowest and highest when in the intermediate position, for example.

Referring to FIGS. 2B and 2C, the keypad 174 comprises one or more domes 240 located between the magnet(s) 210 and the magnetic field sensor(s) 220. A dome 240 collapses when the corresponding button 204 is pressed. Pressing a button 204 causes the dome 240 to bend down such that the dome 240 is located closer to a corresponding magnetic field sensor 220. In some aspects, the dome 240 also provides tactile and/or audible feedback when the corresponding button 204 is pressed.

In some aspects, a dome 240 has a plurality of levels of resistance, such as a high level of resistance and a low level of resistance (including no resistance), and a plurality of positions, such as initial, intermediate, and final positions. The magnets 210 and buttons 204 may have similar positions as the domes 240. In some aspects, a button 204 comprises a plurality of positions (as discussed in more detail below). The dome 240 may have a high level of resistance when in the initial position. In some aspects, in the initial position, the dome 240 initially receives a force from, e.g., a button 204, where the button 204 receives a force from a user's finger. This high level of resistance corresponds to when the dome 240, magnet 210, and button 204 are between the initial and intermediate positions. In some aspects, the dome 240 has a high level of resistance when in the initial position. After the dome 240 receives more force from the button 204, the dome 240 may have a low level of resistance, corresponding to when the dome 240, magnet 210, and button 204 are between the intermediate and final positions. In some aspects, the dome 240 has a low level of resistance when in the final position. When the user releases the button 204, the dome 240 returns back to its initial position where the dome 240 has a high level of resistance, causing a click that provides tactile and/or audible feedback. In some aspects, the click occurs when the dome 240 is switching from a low level of resistance to a high level of resistance and/or when at the intermediate position.

A controller 176 (shown in FIG. 2B) determines whether a button 204 has been pressed and/or released. The functions associated with a button press and/or a button release comprise changing the camera head settings, such as the brightness of the light source, the operation mode such as picture capture mode or video capture mode, etc. The controller 176 receives a signal (e.g., a sensor voltage output) from one or more magnetic field sensors 220 and determines whether a button 204 was pressed based on the corresponding signal. For example, the keypad 174 of the camera head 173 may comprise four buttons 204, and the controller 176 may receive four separate signals, one for each button 204. In some aspects, each of the plurality of buttons 204 is associated with independent steps for detecting a button press and/or a button release (e.g., receiving, determining, and identifying steps, discussed in more detail below).

In some aspects, the keypad 174 is an endoscopic camera head keypad. The keypad 174 may be located in a recess of a camera enclosure 250 (shown in FIGS. 2B and 2C). In some aspects, the keypad 174 is located outside the camera enclosure 250, and circuitry for the camera head 173 (e.g., magnetic field sensor 220 and corresponding wires) is located in the camera enclosure 250. The camera enclosure 250 may seal the internal wiring, enclosing the camera head 173 and allowing the camera head 173 (including the keypad 174) to be autoclavable. The camera enclosure 250 comprises a material that has magnetic permeability so that magnetic fields from the magnet 210 can pass through the material and reach the magnetic field sensor 220. For example, the camera enclosure material comprises, but is not limited to, aluminum.

Aspects of the disclosure comprise accurately detecting a button press and/or a button release and reducing phantom button presses (e.g., when a button has not been pressed or released, but the button press detection system registers a button press or release; or when a button has been pressed or released, but the button press detection system does not register the button press or release) by determining a change in the sensor voltage output from the magnetic field sensor 220 and identifying a spike in the sensor voltage change. A spike may occur when the slope of the sensor voltage has a magnitude that is greater than a slope threshold. For example, a slope of the sensor voltage having a first orientation is registered as a button press, and a slope having a second orientation is registered as a button release. This is unlike methods where a button press and/or a button release is determined by comparing the sensor voltage to a voltage threshold, rather than identifying a spike and/or using slope information.

Figure 3A:
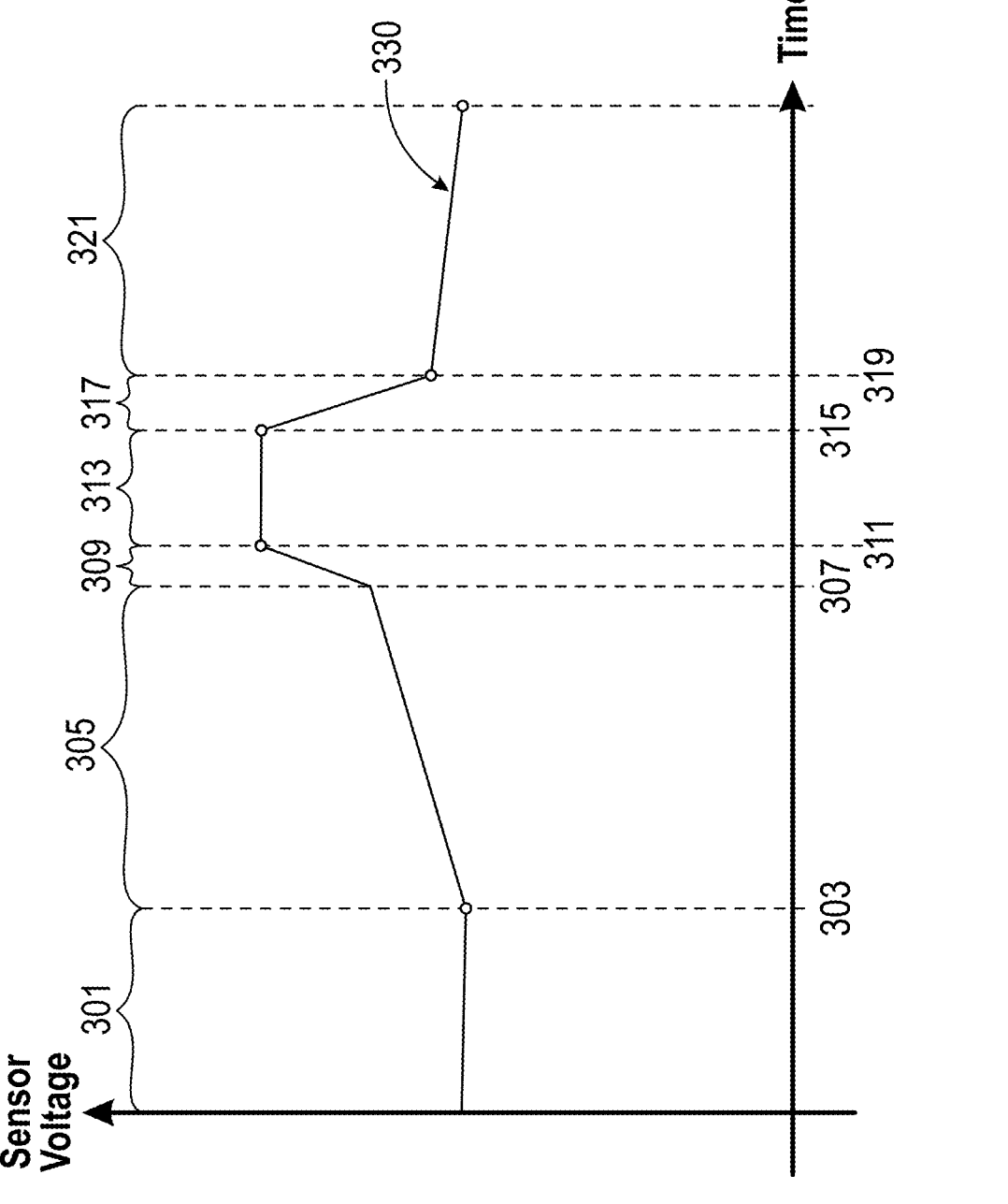
FIG. 3A illustrates a plot of an example operation of a button detection system, according to some aspects.

FIG. 3A illustrates a plot of an example operation of a button detection system, according to some aspects. The plot shows the sensor voltage 330 output by a magnetic field sensor 220 as a user presses and releases a button 204. During time period 301, the button 204 has not been pressed, so the sensor voltage 330 is constant. The dome 240 and magnet 210 are located in their initial positions, which may be the positions when the corresponding button 204 is not pressed. In some aspects, at the initial position, the magnetic field sensor 220 does not measure any amount of magnetic flux or measures a constant amount of magnetic flux.

At time 303, the user begins pressing the button 204. As the user applies increasing force on the button 204, the magnet 210 within the button 204 moves closer to the magnetic field sensor 220 causing the sensor voltage 330 to increase, as shown during time period 305. In some aspects, the magnet 210 moving closer to the magnetic field sensor 220 may cause the sensor voltage 330 to decrease. The dome 240 provides a high level of resistance during time period 305 (when the button 204 is between the initial position and the intermediate position). This high level of resistance causes the magnet 210 to move slowly towards the magnetic field sensor 220 (low velocity), causing the sensor voltage 330 from the magnetic field sensor 220 to have a low slope. A low slope of the sensor voltage 330 comprises a non-zero magnitude that is less than a slope threshold. In some aspects, the low slope does not indicate a button press or a button release.

At time 307, the dome 240 collapses, changing to a low level of resistance. The collapse of the dome 240 and low level of resistance causes the magnet 210 to move rapidly toward the magnetic field sensor 220 (high velocity), leading to a rapid change in the sensor voltage 330 during time period 309. The magnetic field sensor 220 experiences a rapid change in the amount of magnetic flux, and this is shown by a high slope (e.g., relative to the low slope during time period 305) in the plot of FIG. 3A. The high slope corresponds to a spike in the sensor voltage change. The spike comprises a slope of the sensor voltage 330 having a magnitude that is greater than a slope threshold. The spike occurs when the button 204 is between an intermediate position and a final position.

A controller 176 detects a spike (high slope having a first orientation) in the sensor voltage 330 and registers the spike as a button press. Once the button 204 has reached the final position (e.g., the center portion of the dome 240 is touching the camera enclosure 250), the magnet 210 may not be able move any closer to the magnetic field sensor 220, and the sensor voltage 330 from the magnetic field sensor 220 stops increasing (at time 311). If the user continues to press down on the button 204 during time period 313, the sensor voltage 330 remains constant, and the slope of the sensor voltage 330 is zero.

Although FIG. 3A illustrates the sensor voltage 330 having a positive slope (during time period 309) when the spike is registered as a button press, aspects of the disclosure comprise the sensor voltage 330 having a negative slope as the first orientation for registering a button press. The negative slope in the sensor voltage 330 (during time period 317) shown in FIG. 3A for registering a button release is also exemplary. Aspects of the disclosure comprise a positive slope in the sensor voltage 330 for registering a button release.

In some aspects, an endoscopic system 120 comprises one or more compressed springs located under the keypad 174; the spring(s) uncompress(es) when the dome 240 collapses to help the rapid movement of the magnet 210 closer to the magnetic field sensor 220. The change in resistance in the dome 240 (e.g., at the intermediate position) may provide tactile and/or audible feedback to the user. For example, the dome 240 may create a clicking sound.

At time 315, the user stops pressing down on the button 204, causing the dome 240 and magnet 210 to start returning to their initial positions. As the dome 240 and magnet 210 move away from the magnetic field sensor 220, the amount of magnetic flux measured by the magnetic field sensor 220 and corresponding sensor voltage 330 decreases. In some aspects, the dome 240 and magnet 210 moving away from the magnetic field sensor 220 may cause the corresponding sensor voltage 330 to increase. During time period 317, there is a low level of resistance from the dome 240, and thus, the sensor voltage 330 decreases (or increases) rapidly. The button 204 may be located between the final and intermediate positions during this time. The controller 176 detects a spike (high slope having a second orientation) in the sensor voltage 330 and registers the spike as a button release. After that, the dome 240 provides a high level of resistance, starting at time 319, when the button 204 is at the intermediate position. The dome 240 continues to provide this high level of resistance during the time period 321, until the dome 240 and magnet 210 have reached their initial positions. In some aspects, the dome 240 provides tactile and/or audible feedback at time 319 when switching from a low level of resistance to a high level of resistance.

FIG. 3B illustrates a flowchart of an example method for detecting a button press and/or a button release on a keypad 174 of a camera head 173, according to some aspects. The method 350 comprises receiving a sensor voltage 330 from a magnetic field sensor 220 in step 352. In step 354, a controller 176 determines a change in the sensor voltage 330 over time. In step 356, the button 204 receives a force applied by a user's finger. In some aspects, the button 204 may be in its initial position before step 356. During step 356, the dome 240 may provide a high level of resistance (e.g., at time 303 in FIG. 3A), the magnet 210 has a low velocity, and the controller 176 identifies a spike comprising a low slope of the sensor voltage 330 having a non-zero magnitude that is less than a slope threshold (e.g., during time period 305 in FIG. 3A).

In step 358, the dome 240 collapses, and its resistance level switches from a high level of resistance to a low level of resistance (e.g., at time 307 in FIG. 3A). Between steps 356 and 358, the dome 240 may be at the intermediate position. The button 204 is still receiving an applied force (e.g., during time period 309 in FIG. 3A), and the controller 176 identifies a spike comprising a slope of the sensor voltage 330 having a magnitude greater than a slope threshold. One non-limiting example slope threshold is 0.05 V/ms. The slope in step 358 (corresponding to a spike and/or a button press) may be greater than the slope in step 356 (corresponding to a low slope). Aspects of the disclosure comprise the controller 176 continuously determining whether there is a spike in the sensor voltage change.

As the user continues to apply a force on the button 204, the button 204 reaches its final position (e.g., at time 311 in FIG. 3A). In step 360, the controller 176 starts a timer to begin counting how long the button 204 is in its final position (e.g., during time period 313). The final position may be determined based on the slope of the sensor voltage 330, such as the sensor voltage 330 remaining constant (zero slope of the sensor voltage 330). In step 362, the controller 176 continuously determines the change of the sensor voltage (sensor voltage change) over time to determine whether the button 204 has been released. In step 364, the controller 176 determines that the button 204 has been pressed and registers the button press (e.g., when the timer reaches a threshold period of time indicating that a button has been pressed).

Certain events may cause the controller 176 to register the button press. One example event includes the slope of the sensor voltage 330 having a first orientation (positive or negative depending on, for example, the polarity of the magnet 210) and the spike being identified (e.g., during time period 309 or at time 311 in FIG. 3A). Another example event is when the slope of the sensor voltage 330 has a first orientation and the button 204 is in a final position (e.g., at time 311, during time period 313, or at time 315 in FIG. 3A). Similarly, a button release may be registered when the slope of the sensor voltage 330 has a second orientation (negative or positive depending on, for example, the polarity of the magnet 210) and a spike is identified (e.g., during time period 317 or at time 319 in FIG. 3A). Additionally or alternatively, a button release may be registered when the slope of the sensor voltage 330 has a second orientation and the button is in an initial position (e.g., when the spike is identified during time period 317 or at time 319 in FIG. 3A). In this manner, problems associated with button detection systems that determine whether a button is pressed based on a comparison of the sensor voltage 330 against a voltage threshold are avoided or minimized. For example, the keypad 174 and associated buttons 204 of the disclosure may be able to more accurately detect button presses and/or button releases, where fewer phantom button presses (including a button 204 that has not been fully pressed or was accidentally pressed) are registered. The keypad 174 and associated buttons 204 of the disclosure further provide the user with audible and/or tactical feedback, giving the user an indication as to whether or not a button 204 was pressed.

Figure 4:
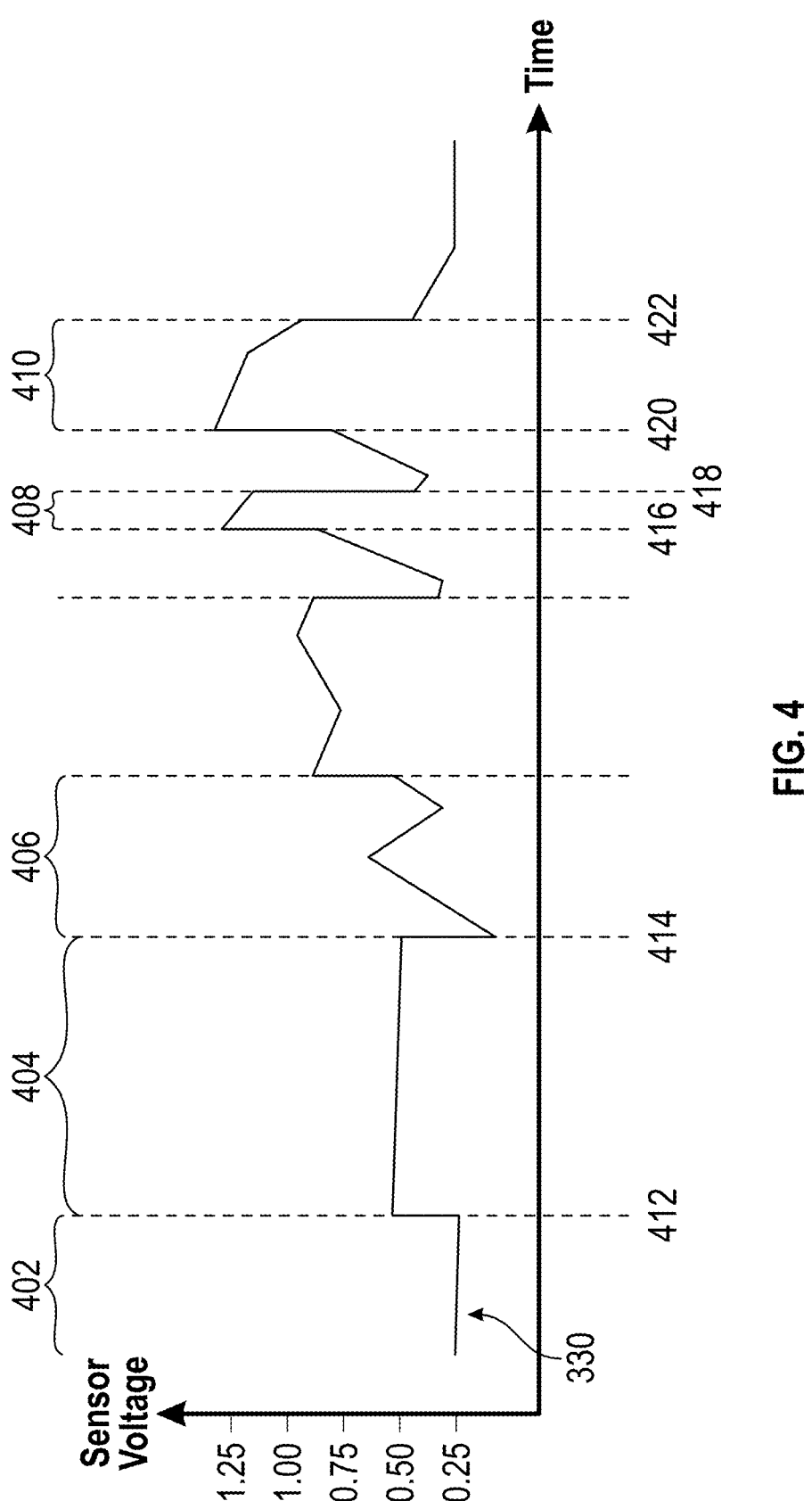
FIG. 4 illustrates a plot of an example operation of a button detection system, according to some aspects.

FIG. 4 illustrates a plot of an example operation of a button detection system, according to some aspects. The plot shown in the figure illustrates the sensor voltage 330. During time period 402, the sensor voltage 330 is around 0.25 V, and the controller 176 determines the button 204 has not been pressed. Then at time 412, the sensor voltage 330 rapidly changes to 0.50 V. The controller 176 determines the button 204 has been pressed because of this rapid change (slope having a first orientation and a magnitude greater than the slope threshold). During time period 404, the controller 176 determines that the button position is the same as the position at time 412 based on the slope of the sensor voltage 330 being zero. At time 414, the sensor voltage 330 rapidly changes back to approximately 0.25 V, and the controller 176 determines the button 204 has been released (the button 204 has returned back to its initial position). In this manner, the controller 176 determines the button 204 was pressed at time 412 based on identifying a spike, associated with a slope having a first orientation, in the sensor voltage 330. The controller 176 also determines the button 204 was released at time 414 based on detecting a spike, associated with a slope of the sensor voltage 330 having a second orientation.

During time period 406, the sensor voltage 330 changes: first from 0.25 V to around 0.6 V, then down to about 0.4 V. Although the sensor voltage 330 changed from 0.25 V to 0.6 V, the change is not rapid enough (e.g., the slope of the sensor voltage 330 does not have a magnitude greater than the slope threshold) to cause the controller 176 to register a button press. This slow increase in sensor voltage 330 may indicate that the dome 240 has not collapsed, but the sensor voltage change was instead due to, e.g., a phantom button press. This is unlike button detection systems where the sensor voltage change may have been incorrectly registered as a button press due to the sensor voltage 330 being greater than a voltage threshold, such as 0.5 V. Similarly, this slow decrease in sensor voltage 330 from 0.6 V to 0.4 V (or 0.4V to 0.6V) is not registered as a button release by the controller 176 of the present disclosure but may be incorrectly registered by the button detection systems that determine a button press and/or a button release based on voltage threshold. By determining whether or not a button has been pressed or released based on the sensor voltage change, aspects of the disclosure may avoid or reduce false positives.

Although FIG. 4 illustrates the sensor voltage 330 having a positive slope (at time 412, for example) for registering a button press and a negative slope in the sensor voltage 330 (at time 414) for registering a button release, the orientations of the slopes are exemplary, and other examples are included in the present disclosure. The orientation for a button press and/or a button release may depend on the polarity of the magnet 210, for example. In some aspects, the sensor voltage 330 may have a negative slope as the first orientation for registering a button press and a positive slope in the sensor voltage 330 for registering a button release.

Aspects of the disclosure comprise an endoscopic system 120 capable of receiving different types of button presses, such as a short press, a long press, and a press-and-hold press. Different button presses may be used for different functions, for example. The controller 176 may distinguish between the different types of presses based on the duration of when the sensor voltage change is zero and/or the sensor voltage 330 is constant, e.g., relative to a duration threshold.

A short press may be registered when the controller 176 identifies a first spike (such as the quick button press at time 416) followed by a short hold of the button 204 (such as during time period 408), and then a second spike (quick button release at time 418) shortly after. The first spike may comprise a high slope (magnitude greater than a slope threshold) having a first orientation, and the second spike may comprise a high slope having a second orientation. For example, the first orientation and the second orientation may correspond to a positive slope and a negative slope, respectively. Alternatively, the first orientation and the second orientation may correspond to a negative slope and a positive slope, respectively. A short hold of the button 204 may occur when the duration between the first spike and the second spike is less than a short press duration threshold (e.g., as measured by a timer set by controller 176). The short press duration threshold may be 50 milliseconds, and the duration of time period 408 is less than the short press duration threshold of 50 milliseconds. In some aspects, the controller 176 determines whether or not the button press is a short press when the button is released (e.g., at time 418). When the controller 176 registers the button press as a short press, the camera head 173 performs a corresponding function such as taking a picture.

FIG. 4 also illustrates an example long press, as shown during time period 410. A long press may occur when the controller 176 identifies a first spike (quick button press at time 420) followed a second spike (quick button release at time 422), where the duration between the first spike and the second spike (time period 410) is greater than the short press duration threshold but less than the long press duration threshold (e.g., as measured by the timer set by controller 176). The first spike comprises a high slope of the sensor voltage 330 having a first orientation. The second spike comprises a high slope of the sensor voltage 330 having a second orientation. The long press duration threshold may be 500 milliseconds, for example. In some aspects, the controller 176 determines whether the button press is a long press when the button is released (e.g., at time 422), after the duration is longer than short press duration threshold or before the duration is longer than the long press duration threshold. One example function that is activated with a long press is recording a video.

Additionally or alternatively, aspects of the disclosure may include a press-and-hold press. As one non-limiting example, a press-and-hold press may cause the endoscopic system 120 to open up an on-screen menu on, e.g., the display screen 175. A press-and-hold press occurs when the user presses the button 204 for a duration longer than for the long press duration threshold (e.g., as measured by the timer set by controller 176). For example, the controller 176 may register the button press during time period 404 in FIG. 4 as a press-and-hold press. As shown in the figure, a press-and-hold press comprises a slope of the sensor voltage 330 (at time 412) having a first orientation followed by zero or low slope during time period 404, and then a slope having a second orientation afterwards at time 414. In some aspects, the controller 176 determines whether the type of button press is a press-and-hold press when the button is released (e.g., at time 414) and/or after the duration is longer than a long press duration threshold. In response to registering a press-and-hold press, the controller 176 may allow the user to navigate the on-screen menu after releasing the button, e.g., at time 414.

In some aspects, the controller 176 may use the sensor voltage 330 (in some instances, in addition to the sensor voltage change) to determine, or help determine, the type of button press. After identifying a spike, the controller 176 may compare the sensor voltage 330 to a voltage threshold to determine whether or not the button is being pressed (e.g., the magnet 210 is within a certain distance from the magnetic field sensor 220). In some aspects, this comparison of the sensor voltage 330 to the voltage threshold is made by the controller 176 after determining that the button 204 has been pressed. If the sensor voltage 330 meets a certain criteria, such as being greater than a voltage threshold or being less than a voltage threshold, then the controller 176 may determine that the button press has continued. The duration of this continued button press indicates the type of press: shorter than a short press duration threshold (e.g., less 50 milliseconds) for a short press, longer than a short press duration threshold but shorter than a long press duration threshold (e.g., between 50-500 milliseconds) for a long press, or longer than a long press duration threshold (e.g., longer than 500 milliseconds) for a press-and-hold press. The duration of a continued button press may be determined based on the duration between a button press and a button release (e.g., as measured by the timer set by controller 176). In some aspects, a button release occurs when the sensor voltage 330 drops below the voltage threshold (or above the voltage threshold) and/or the slope of the sensor voltage changes from zero to negative/positive, or negative/positive to zero.

In some instances, continuously using a pre-determined threshold may lead to inaccurate detection of a button press and/or a button release. A pre-determined threshold may not account for changes to the keypad 174, such as decays in magnetic flux that occur over time due to the thermal cycling of the magnet 210 or a shift in the position of the magnet 210 (e.g., due to dropping the camera head 173). Aspects of the disclosure may comprise dynamically adjusting the slope threshold or voltage threshold used for determining a button press and/or a button release. For example, the controller 176 determines a baseline voltage or slope when powering on the endoscopic system 120 and adjusts the slope threshold or voltage threshold based on the baseline voltage or slope, such as when the baseline slope or voltage differs from the slope threshold or voltage threshold. The baseline slope or voltage may be the sensor voltage 330 or corresponding slope when the button is not pressed (in its initial position); for example, a sensor voltage 330 of 0.25 V during time period 402 when the button is not pressed in FIG. 4 is the baseline voltage.

Figure 8:
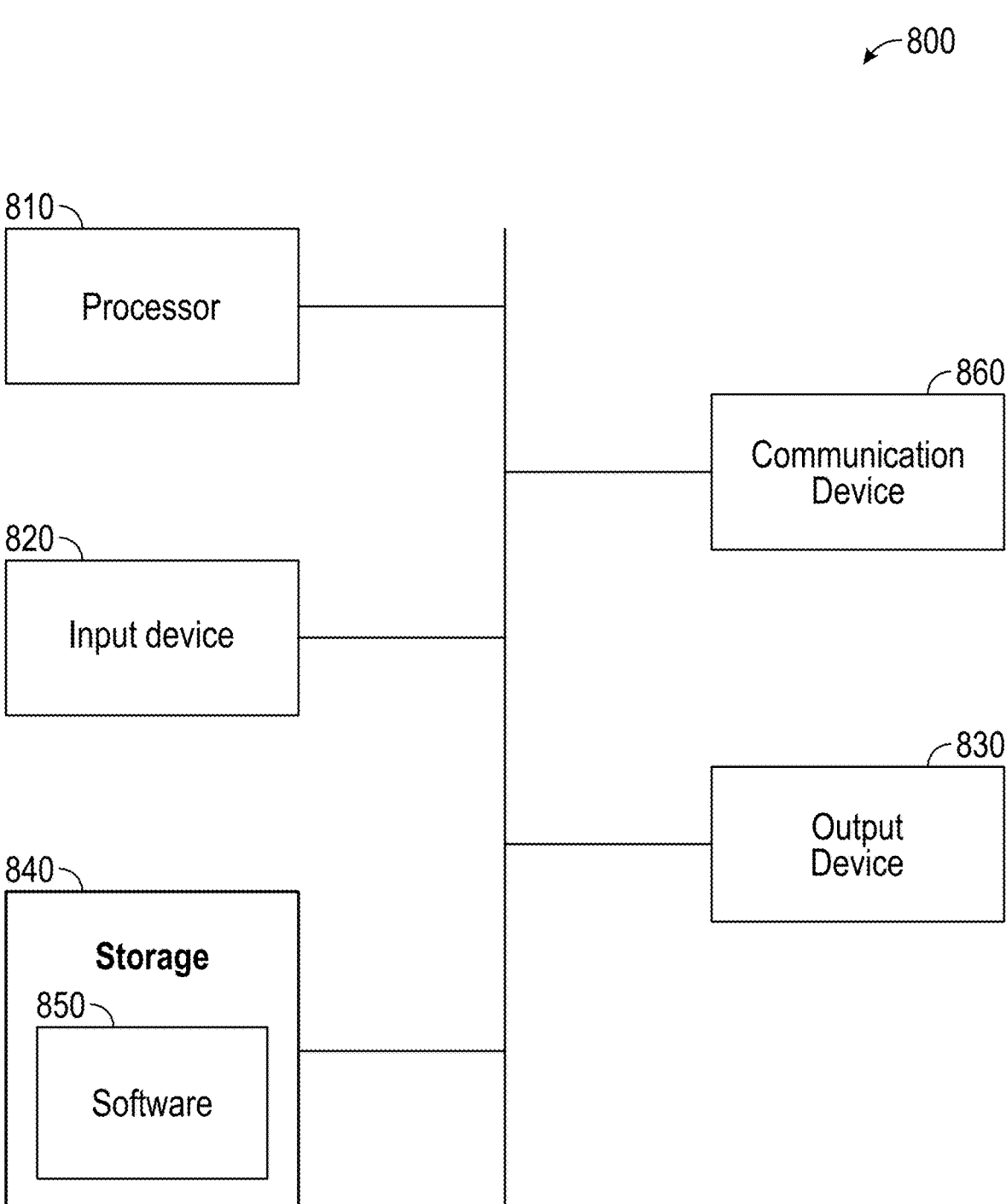
FIG. 8 illustrates an example computing system, according to some aspects.

In some aspects, the endoscopic system 120 uses and/or trains a machine-learning model (e.g., stored in storage 840 and executed by processor 810 shown in FIG. 8) to adjust the slope threshold or the voltage threshold for accurately differentiating between button presses, button releases, and phantom button presses. The machine-learning model may determine the slope or voltage threshold based on training data. In some aspects, the training data comprises a plurality of different button presses, a plurality of different button releases, and/or corresponding sequences, such as the sequence shown in FIG. 4. In some aspects, the machine-learning model determines how much the slope threshold or the voltage threshold has changed (e.g., based on the average change from the pre-determined threshold) and updates the pre-determined threshold accordingly.

Aspects of the disclosure comprise different slopes or voltage thresholds for different buttons 204. As one non-limiting example, the buttons 204 of a keypad 174 have different sized domes, for example, 10 mm, 15 mm, etc. A first button 204 may have a first slope or voltage threshold, while a second button 204 may have a second slope or voltage threshold.

Figure 5:
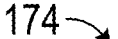
FIG. 5 illustrates an example keypad comprising a plurality of buttons, according to some aspects.

In some instances, it may be desirable to place the buttons 204 in close proximity to one another so that, e.g., the keypad 174 comprises a greater number of buttons 204 without requiring the keypad 174 be large or bulky (due to requiring large spacing between the buttons 204). FIG. 5 illustrates an example keypad 174 comprising a plurality of buttons: four buttons 204N and one button 204P. The buttons 204 on the keypad 174 may be located in close proximity to each other (closely-spaced buttons). To avoid or reduce crosstalk between magnetic flux lines of magnets 210 located close to each other, aspects of the disclosure comprise at least two (e.g., neighboring) magnets 210 having different polarities. For example, the magnets 210 of buttons 204N may have a first polarity, and the magnet 210 of button 204P may have a second polarity. The second polarity may be opposite the first polarity. In some aspects, each magnet 210 is magnetically coupled to a magnetic field sensor 220. The magnetic field sensors 220 may be omnipolar magnetic field sensors configured to detect positive magnetic flux, negative magnetic flux, or both. The magnetic field sensor 220 of button 204P may not be magnetically coupled to the magnets 210 of the neighboring buttons 204N. Aspects of the disclosure comprise the controller 176 determining whether a button press is associated with a first button 204N or a second button 204P based on the orientation (negative or positive) of the slope of the sensor voltage 330.

When the user presses or releases one of the first buttons 204N, the corresponding magnetic field sensor 220 generates a sensor voltage 330 having a first polarity and registers a button press and/or a button release for the first button 204N. When the user presses or releases the second button 204P, its corresponding magnetic field sensor 220 generates a second sensor voltage 330 having a second polarity and registers a button press and/or a button release for the second button 204P. The second polarity of the sensor voltage 330 for the second button 204P may be different (e.g., opposite) than the first polarity of the sensor voltage 330 for the first button 204N. The controller 176 distinguishes between button presses and/or button releases of different buttons based on the polarity of the sensor voltage 330. In this manner, the amount of crosstalk between neighboring buttons and magnets may be reduced, and neighboring button presses are accurately registered.

Figure 6A:
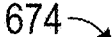
FIG. 6A and FIG. 6B illustrate top and cross-sectional views, respectively, of an example keypad comprising a magnetic field sensor that magnetically couples to a plurality of magnets, according to some aspects.

Although FIGS. 2A-2C and 5 illustrate a keypad 174 having a unique magnetic field sensor 220 for each button 204, aspects of the disclosure comprise a keypad having a greater number of buttons 204 and/or magnets 210 than magnetic field sensors 220. FIGS. 6A and 6B illustrate top and cross-sectional views, respectively, of an example keypad 674 comprising a magnetic field sensor 620 that magnetically couples to a plurality of magnets 210A and 210B, according to some aspects. The keypad 674 comprises a plurality of buttons 604A and 604B. Each button 604 may comprise a magnet 210 and a dome 240 (for example, button 604A comprises a magnet 210A and a dome 240A, and button 604B comprises a magnet 210B and a dome 240B). The plurality of buttons 604A and 604B magnetically couples to the same magnetic field sensor 620. The camera enclosure 250 is located between the domes 240A and 240B and the magnetic field sensor 620. In some aspects, the controller 176 determines whether a button press and/or a button release corresponds to the first button 604A or the second button 604B based on the slope of the sensor voltage 330. A button press and/or a button release of a first button 604A corresponds to a first slope, while a button press and/or a button release of a second button 604B corresponds to a second slope, for example. The different first and second slopes may be due to the first and second buttons 604A and 604B having different properties (e.g., size, resistance). In this manner, a button press and/or a button release for the first button 604A may be differentiated from a button press and/or a button release for the second button 604B.

Figure 7A:
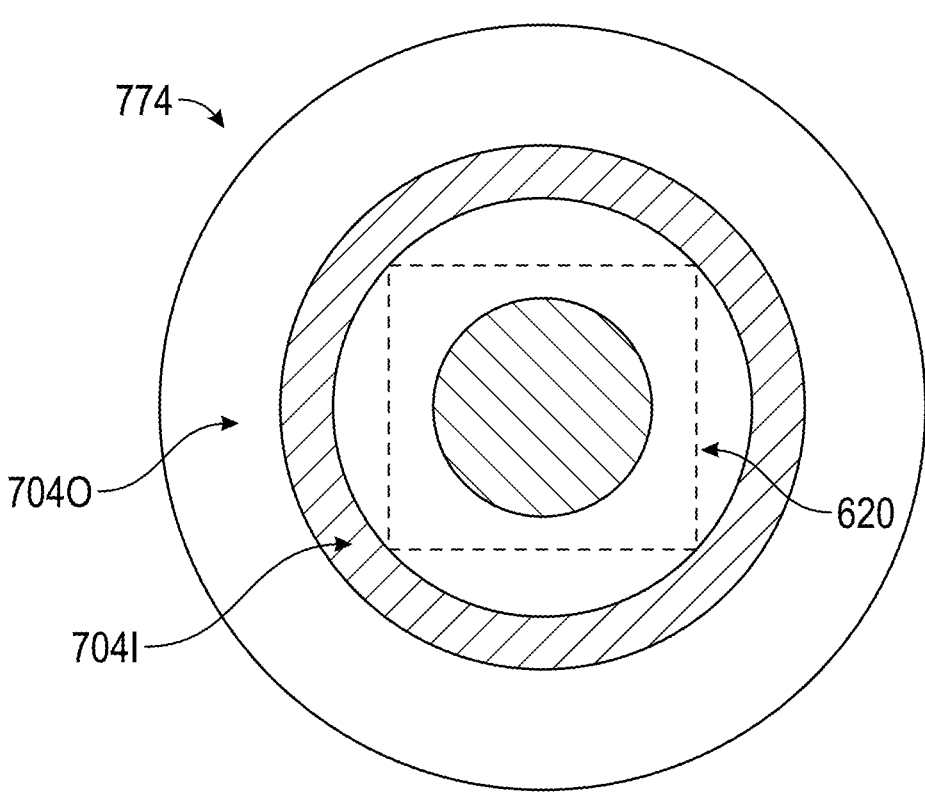
FIG. 7A and FIG. 7B illustrate top and cross-sectional views, respectively, of an example keypad comprising concentric buttons, according to some aspects.
Figure 7B:
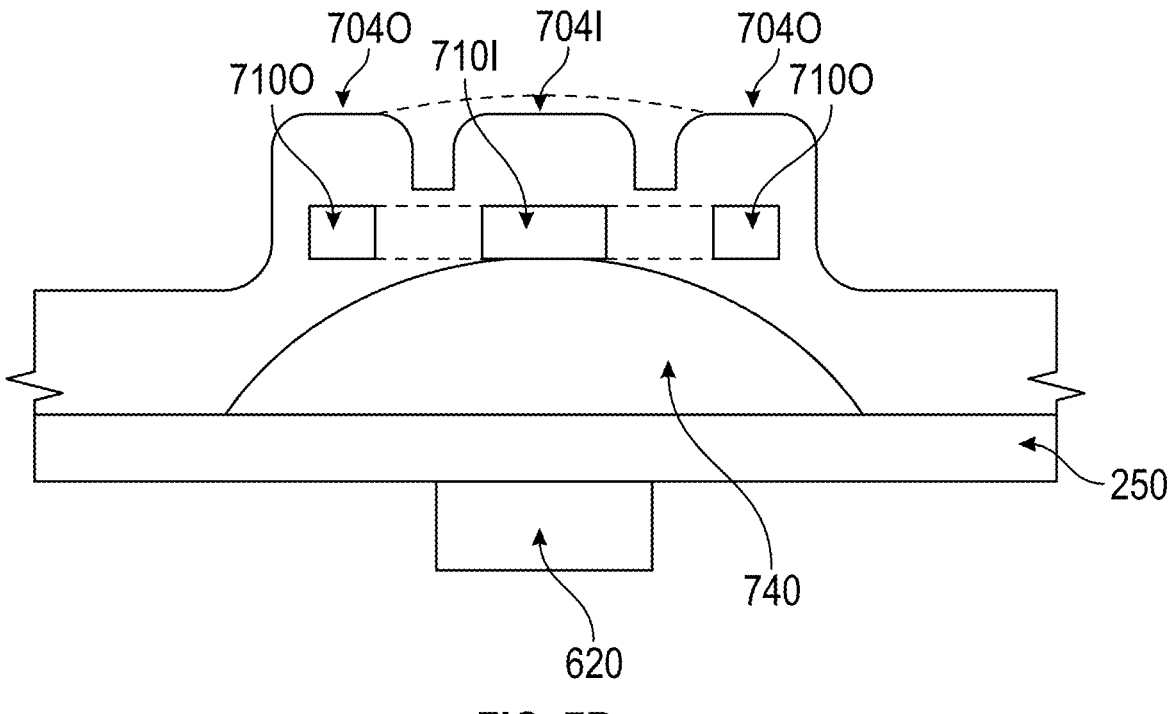

Aspects of the disclosure comprise other button configurations such as split buttons (e.g., a left half-circle shaped button and a right half-circle shaped button) or concentric buttons. FIGS. 7A and 7B illustrate top and cross-sectional views, respectively, of an example keypad comprising concentric buttons, according to some aspects. The keypad 774 comprises a plurality of buttons 704I and 704O, a plurality of magnets 710I and 710O, a dome 740, and a magnetic field sensor 620. The inner button 704I comprises the inner magnet 710I, and the outer button 704O comprises the outer magnet 710O. In some aspects, the plurality of magnets 710 comprises concentric magnets. Both the inner button 704I (and corresponding inner magnet 710I) and outer button 704O (and corresponding outer magnet 710O) cause movement of the dome 740 towards or away from the magnetic field sensor 620 when pressed or released, respectively.

In some aspects, the outer magnet 710O has a different magnetic force than the inner magnet 710I. For example, the outer magnet 710O is stronger (higher magnetic force) than the inner magnet 710I. When the outer button 704O is pressed, the slope of the sensor voltage 330 may be higher than when the inner button 704I is pressed due to the stronger magnetic force for the outer magnet 710O. In some aspects, the controller 176 is able to distinguish between a button press and/or a button release of the inner button 704I and a button press and/or a button release of the outer button 704O by way of different sensor voltage changes. For example, a first sensor voltage change indicates a button press of the outer button 704O, while a second sensor voltage change indicates a button press of the inner button 704I. The first sensor voltage change may be greater than the second sensor voltage change.

Figure 6A:
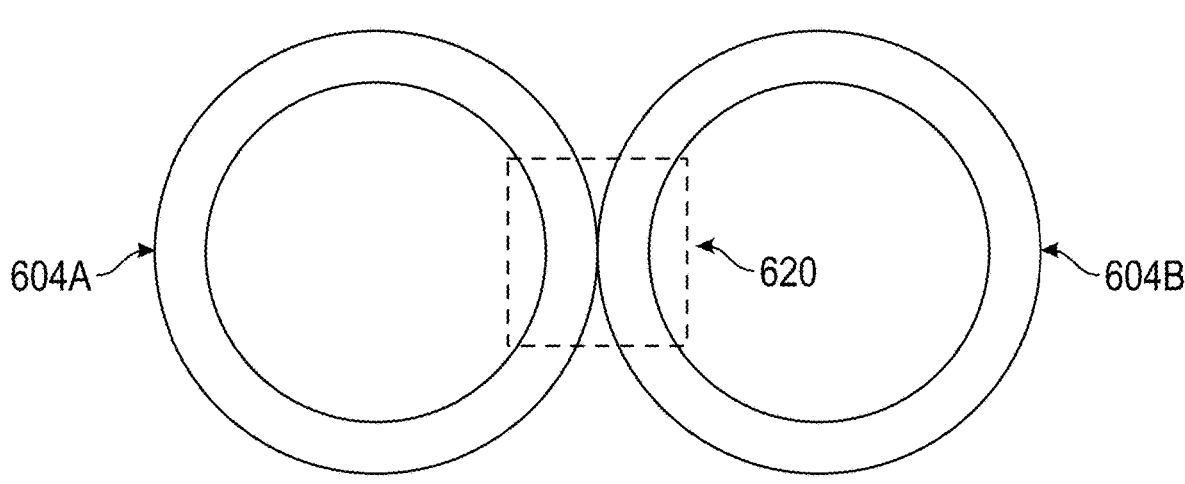
Figure 6B:
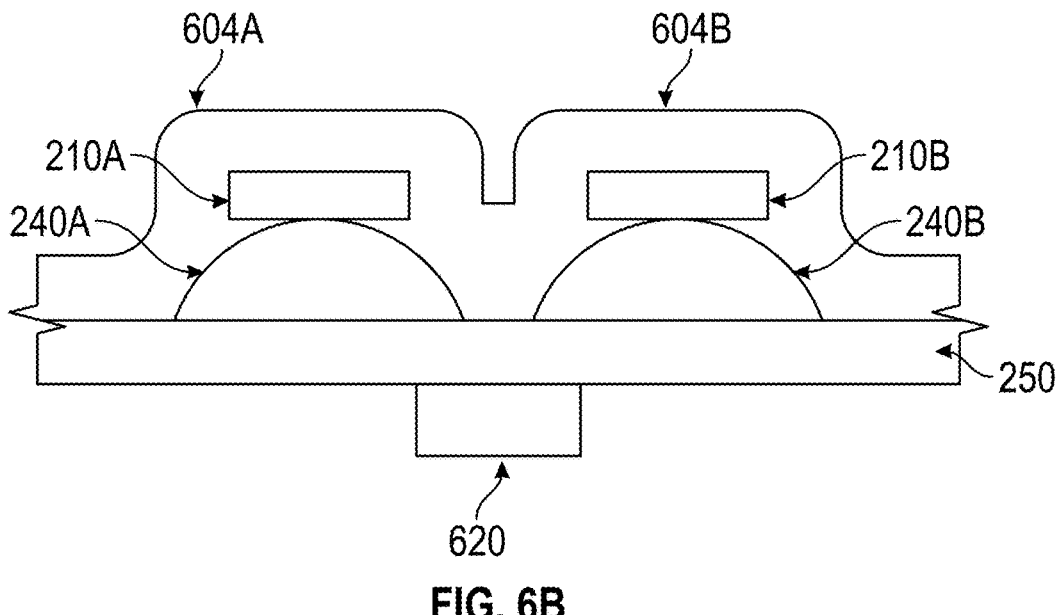

FIG. 8 illustrates an example computing system, in accordance with some examples, that can be used for performing any of the methods described herein, including method 350 of FIG. 3B, and can be used for any of the systems described herein, including the endoscopic system 120 of FIG. 1, a camera head 173 comprising keypads 174 of FIG. 2A-2C or 5, and/or a camera head 173 comprising keypads 674 or 774 of FIG. 6 or 7, respectively. System 800 can be a computer coupled to a network, which can be, for example, an operating room network or a hospital network. System 800 can be a client computer or a server. As shown in FIG. 8, system 800 can be any suitable type of controller (including a microcontroller) or processor (including a microprocessor) based system, such as an embedded control system, personal computer, workstation, server, or handheld computing device (portable electronic device) such as a phone or tablet. The system can include, for example, one or more of processor 810, input device 820, output device 830, storage 840, or communication device 860.

Input device 820 can be any suitable device that provides input, such as a touch screen, keyboard or keypad, mouse, gesture recognition component of a virtual/augmented reality system, or voice-recognition device. Output device 830 can be or include any suitable device that provides output, such as a touch screen, haptics device, virtual/augmented reality display, or speaker.

Storage 840 can be any suitable device that provides storage, such as an electrical, magnetic, or optical memory including a RAM, cache, hard drive, removable storage disk, or other non-transitory computer readable medium. Communication device 860 can include any suitable device capable of transmitting and receiving signals over a network, such as a network interface chip or device. The components of the computer can be coupled in any suitable manner, such as via a physical bus or wirelessly.

Software 850, which can be stored in storage 840 and executed by processor 810, can include, for example, the programming that embodies the functionality of the present disclosure (e.g., as embodied in the devices as described above). For example, software 850 can include one or more programs for performing one or more of the steps of the methods disclosed herein.

Software 850 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 840, that can contain or store programming for use by or in connection with an instruction execution system, apparatus, or device.

Software 850 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic, or infrared wired or wireless propagation medium.

System 800 may be coupled to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 800 can implement any operating system suitable for operating on the network. Software 850 can be written in any suitable programming language, such as C, C++, C#, Java, or Python. In various examples, application software embodying the functionality of the present disclosure can be deployed in different configurations, such as in a client/server arrangement or through a Web browser as a Web-based application or Web service, for example.

The foregoing description, for the purpose of explanation, has been described with reference to specific aspects. However, the illustrative discussions above are not intended to be exhaustive or to limit the invention to the precise forms disclosed. Many modifications and variations are possible in view of the above teachings. The aspects were chosen and described in order to best explain the principles of the techniques and their practical applications. Others skilled in the art are thereby enabled to best utilize the techniques and various aspects with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method of detecting a button press and/or a button release of a button on a camera head, the method comprising:

receiving a sensor voltage from a magnetic field sensor;

determining a change of the sensor voltage over time; and identifying a spike comprising a slope of the sensor voltage having a magnitude greater than a slope threshold, wherein the spike indicates the button press and/or the button release.

2. The method of claim 1, further comprising:

registering the button press when the slope of the sensor voltage has a first orientation, and the spike is identified or the button is in a final position; or registering the button release when the slope of the sensor voltage has a second orientation, and the spike is identified or the button is in an initial position.

3. The method of claim 1, wherein the spike occurs when:

the button is between an intermediate position and a final position;

a magnet associated with the button has a high velocity; or a dome associated with the button has a low level of resistance, wherein the dome comprises the low level of resistance and a high level of resistance.

4. The method of claim 1, further comprising:

identifying a low slope of the sensor voltage comprising a non-zero magnitude less than the slope threshold, wherein the low slope:

does not indicate the button press and/or the button release;

occurs when a dome associated with the button has a high level of resistance, wherein the dome comprises a low level of resistance and the high level of resistance;

occurs when a magnet associated with the button has a low velocity; or when the button is between an initial position and an intermediate position.

5. The method of claim 1, further comprising:

determining a position of the button based on the slope of the sensor voltage, wherein the position of the button comprises an initial position, an intermediate position, and a final position.

6. The method of claim 1, further comprising:

identifying a second spike in the sensor voltage change, wherein the second spike comprises the slope of the sensor voltage having a magnitude greater than the slope threshold and a second orientation; and registering the button press as:

a short press when a duration between the spike and the second spike is shorter than a short press duration threshold;

a long press when a duration between the spike and the second spike is longer than the short press duration threshold and shorter than a long press duration threshold; or a press-and-hold press when a duration between the spike and the second spike is longer than the long press duration threshold.

7. The method of claim 1, wherein the camera head comprises a first button and a second button, the method further comprising:

determining whether the button press corresponds to the first button or the second button based on the slope of the sensor voltage or an orientation of the slope of the sensor voltage.

8. A system comprising a camera head, the system comprising:

a button;

a magnet;

a magnetic field sensor that outputs a sensor voltage indicative of magnetic flux between the magnet and the magnetic field sensor; and a controller configured to:

determine a change of the sensor voltage over time; and identify a spike in the sensor voltage change, wherein the spike comprises a slope of the sensor voltage having a magnitude greater than a slope threshold, wherein the spike indicates a button press and/or a button release.

9. The system of claim 8, wherein the controller is configured to:

register the button press when the slope of the sensor voltage has a first orientation, and the spike is identified or the button is in a final position; or register the button release when the slope of the sensor voltage has a second orientation, and the spike is identified or the button is in an initial position.

10. The system of claim 8, wherein the spike occurs when:

the button is between an intermediate position and a final position; or the magnet has a high velocity.

11. The system of claim 8, further comprising:

a dome located between the magnet and the magnetic field sensor, the dome comprising a low level of resistance and a high level of resistance, wherein the spike occurs when the dome has the low level of resistance.

12. The system of claim 8, further comprising:

a dome located between the magnet and the magnetic field sensor, the dome comprising a low level of resistance and a high level of resistance;

wherein the controller is configured to:

identify a low slope of the sensor voltage comprising a non-zero magnitude less than the slope threshold, wherein the low slope occurs when:

the dome has the high level of resistance;

the magnet has a low velocity; or the button is between an initial position and an intermediate position.

13. The system of claim 8, wherein the button comprises a plurality of positions determined based on the slope of the sensor voltage, where the plurality of positions comprises an initial position, an intermediate position, and a final position.

14. The system of claim 8, wherein the controller is configured to:

identify a second spike in the sensor voltage change, wherein the second spike comprises the slope of the sensor voltage having a magnitude greater than the slope threshold and a second orientation; and register the button press:

when a duration between the spike and the second spike is less than a duration threshold corresponding to a type of button press;

as a short press when a duration between the spike and the second spike is shorter than a short press duration threshold;

as a long press when a duration between the spike and the second spike is longer than the short press duration threshold and shorter than a long press duration threshold; or as a press-and-hold press when a duration between the spike and the second spike is longer than the long press duration threshold.

15. The system of claim 8, wherein the camera head comprises a first button and a second button, wherein the controller is configured to:

determine whether the button press and/or the button release corresponds to the first button or the second button based on the slope of the sensor voltage.

16. The system of claim 8, wherein the camera head comprises one or more buttons and one or more magnetic field sensors, wherein a number of the one or more buttons is the same as a number of the one or more magnetic field sensors.

17. The system of claim 8, wherein the camera head comprises a plurality of buttons and one or more magnetic field sensors, wherein a number of the plurality of buttons is greater than a number of the one or more magnetic field sensors.

18. An apparatus comprising:

a button;

a magnet;

a magnetic field sensor that outputs a sensor voltage indicative of magnetic flux between the magnet and the magnetic field sensor; and a non-transitory computer-readable medium encoding instructions which, when executed by a processor, cause the processor to:

determine a change of the sensor voltage over time; and identify a spike in the sensor voltage change, wherein the spike comprises a slope of the sensor voltage having a magnitude greater than a slope threshold, wherein the spike indicates a button press and/or a button release.

19. The apparatus of claim 18, wherein the non-transitory computer-readable medium cause the processor to:

register the button press when the slope of the sensor voltage has a first orientation, and the spike is identified or the button is in a final position; or register the button release when the slope of the sensor voltage has a second orientation, and the spike is identified or the button is in an initial position.

20. The apparatus of claim 18, wherein the non-transitory computer-readable medium cause the processor to:

identify a second spike in the sensor voltage change, wherein the second spike comprises the slope of the sensor voltage having a magnitude greater than the slope threshold and a second orientation; and register the button press:

when a duration between the spike and the second spike is less than a duration threshold corresponding to a type of button press;

as a short press when a duration between the spike and the second spike is shorter than a short press duration threshold;

as a long press when a duration between the spike and the second spike is longer than the short press duration threshold and shorter than a long press duration threshold; or as a press-and-hold press when a duration between the spike and the second spike is longer than the long press duration threshold.

* * * * *

24